United States Patent
Nguyen et al.

(10) Patent No.: US 11,626,187 B2
(45) Date of Patent: Apr. 11, 2023

(54) SYSTEMS, COMPOSITIONS, AND METHODS FOR DISCOVERY OF MSI AND NEOEPITOPES THAT PREDICT SENSITIVITY TO CHECKPOINT INHIBITORS

(71) Applicant: NantOmics, LLC, Culver City, CA (US)

(72) Inventors: Andrew Nguyen, San Jose, CA (US); Kayvan Niazi, Los Angeles, CA (US); Patrick Soon-Shiong, Los Angeles, CA (US); Stephen Charles Benz, Santa Cruz, CA (US); Shahrooz Rabizadeh, Los Angeles, CA (US)

(73) Assignee: NantOmics LLC, Culver City, CA (US)

(*) Notice: Subject to any disclaimer, the term of this patent is extended or adjusted under 35 U.S.C. 154(b) by 345 days.

(21) Appl. No.: 15/292,021

(22) Filed: Oct. 12, 2016

(65) Prior Publication Data

US 2017/0032082 A1    Feb. 2, 2017

Related U.S. Application Data

(60) Provisional application No. 62/240,494, filed on Oct. 12, 2015.

(51) Int. Cl.

| | | |
|---|---|---|
| *G16B 20/20* | (2019.01) | |
| *G16B 20/00* | (2019.01) | |
| *G16B 30/00* | (2019.01) | |
| *G16H 50/20* | (2018.01) | |
| *G01N 33/574* | (2006.01) | |
| *G01N 33/569* | (2006.01) | |
| *G01N 33/68* | (2006.01) | |
| *G16H 20/40* | (2018.01) | |
| *G16H 70/60* | (2018.01) | |
| *G16B 30/10* | (2019.01) | |

(52) U.S. Cl.
CPC ....... *G16B 20/20* (2019.02); *G01N 33/56977* (2013.01); *G01N 33/574* (2013.01); *G01N 33/6878* (2013.01); *G16B 20/00* (2019.02); *G16B 30/00* (2019.02); *G16B 30/10* (2019.02); *G16H 20/40* (2018.01); *G16H 50/20* (2018.01); *G16H 70/60* (2018.01); *G01N 2333/70532* (2013.01); *G01N 2570/00* (2013.01)

(58) Field of Classification Search
None
See application file for complete search history.

(56) References Cited

U.S. PATENT DOCUMENTS

| 7,473,532 | B2 | 1/2009 | Darfler et al. |
|---|---|---|---|
| 8,207,315 | B2 | 6/2012 | Wang et al. |
| 8,652,473 | B2 | 2/2014 | Johns et al. |
| 2005/0048070 | A1 | 3/2005 | Ditzel et al. |
| 2010/0202968 | A1 | 8/2010 | Nitsch et al. |
| 2010/0203109 | A1 | 8/2010 | Herlyn et al. |
| 2011/0293637 | A1* | 12/2011 | Hacohen ............ C12Q 1/6886 424/173.1 |
| 2012/0059670 | A1 | 3/2012 | Sanborn et al. |
| 2012/0066001 | A1 | 3/2012 | Sanborn et al. |
| 2015/0125463 | A1 | 5/2015 | Cogswell et al. |
| 2016/0101170 | A1 | 4/2016 | Hacohen et al. |
| 2016/0339090 | A1* | 11/2016 | Hacohen ............ A61K 39/0011 |
| 2018/0141998 | A1 | 5/2018 | Nguyen et al. |
| 2019/0099475 | A1 | 4/2019 | Benz et al. |

FOREIGN PATENT DOCUMENTS

| CA | 2 987 730 A1 | 10/2016 |
|---|---|---|
| CA | 2 988 388 A1 | 10/2016 |
| CN | 108513593 A | 9/2018 |
| CN | 108701173 A | 10/2018 |
| EP | 2 279 749 A1 | 2/2011 |
| EP | 3 280 738 A1 | 2/2018 |
| EP | 3 286 361 A1 | 2/2018 |
| EP | 3 362 930 A1 | 8/2018 |
| JP | 2018-513187 A | 5/2018 |
| JP | 2018-532736 A | 11/2018 |
| KR | 10-2018-0087244 A | 8/2018 |
| MX | 2017013613 A | 9/2018 |
| WO | 2011/143656 A2 | 11/2011 |
| WO | 2011/143656 A3 | 8/2012 |
| WO | 2014/052707 A2 | 4/2014 |
| WO | 2015/058159 A1 | 4/2015 |
| WO | 2015/095811 A2 | 6/2015 |
| WO | 2015/103037 A2 | 7/2015 |
| WO | 2016/164833 A1 | 10/2016 |

(Continued)

OTHER PUBLICATIONS

Charoentong et al. (Cancer Immunol. Immunother. (2012) vol. 61:1885-1903).*
Rizvi et al. (Science (2015) Apr. 3, 2015, vol. 348, Issue 6230:124-128).*
Segal et al. (Cancer Res. (2008) vol. 68(3):889-892).*
Castle et al. (Cancer Research (2012) vol. 72:1081-1091).*
Hacohen et al. (Cancer Immunology research (2013) vol. 1, Issue 1:11-15).*
Lundegaard et al. (Nucleic Acids Research (2008) vol. 36:W509-W512).*
Kelderman et al. (Cancer Cell (2015) vol. 28:11-13).*
Lutz et al. (Cancer Immunology Research (2014) vol. 2:OF1-OF4).*
Parmiani et al. (Vaccines (2015) vol. 3:420-428).*

(Continued)

*Primary Examiner* — Lori A. Clow
(74) *Attorney, Agent, or Firm* — Martin Fessenmaier; Umberg Zipser LLP

(57) ABSTRACT

Systems and methods are presented that allow for predicting treatment response of a tumor to a checkpoint inhibitor. In one exemplary aspect, the treatment response is directly associated with a relatively high number of patient- and tumor-specific immunologically visible neoepitopes. Specific mutational patterns in the nucleic acid encoding the neoepitope may be further indicative of treatment response.

14 Claims, 4 Drawing Sheets

Specification includes a Sequence Listing.

(56) References Cited

FOREIGN PATENT DOCUMENTS

| WO | 2016/172722 A1 | 10/2016 |
| WO | 2017/035392 A1 | 3/2017 |
| WO | 2017/066357 A1 | 4/2017 |

OTHER PUBLICATIONS

Van Rooij et al. (Journal of Clinical Oncology (2013) vol. 31:e439-e442).*
Alexandrov et al. (Nature (2013) vol. 500:415-421).*
Warren et al., "Derivation of HLA types from shotgun sequence datasets", Genome Medicine, 2012, vol. 4, No. 12, pp. 1-8.
Liu et al., "ATHLATES: accurate typing of human leukocyte antigen through exome sequencing", Nucleic Acids Research, Jun. 8, 2013, vol. 41, No. 14, pp. 1-8.
Bai et al., "Inference of high resolution HLA types using genome-wide RNA or DNA sequencing reads", BMC Genomics, 2014, vol. 15, No. 325, pp. 1-16.
Amalfitano et al., "Production and Characterization of Improved Adenovirus Vectors with the E1, E2b, and E3 Genes Deleted", Journal of Virology, Feb. 1998, vol. 72, No. 2, pp. 926-933 (Cited from Specification).
Vigneron et al., "Database of T cell-defined human tumor antigens: the 2013 update", Cancer Immunity, Jul. 15, 2013, vol. 13, 6 pages.
Carmen et al., "Concepts in antibody phage display", Briefings In Functional Genomics And Proteomics, Jul. 2002, vol. 1 No. 2, pp. 189-203.
Hosse et al., "A new generation of protein display scaffolds for molecular recognition", Protein Science, Jan. 2006, vol. 15, No. 1, pp. 14-27.
Zhang et al., "Machine Learning Competition in Immunology—Prediction of HLA class I molecules", J Immunology Methods, 2011, vol. 374, p. 1-9 (Cited from Specification).
Van Allen, E. et al., Genomic correlates of response to CTLA-4 blockade in metastatic melanoma, Science, 2015, pp. 207-211, vol. 350.
Fritsch, E. et al., HLA-Binding Properties of Tumor Neoepitoples in Humans, Cancer Immunology Research, 2014, pp. 522-529, vol. 2.
Le, Dung et al., PD-1 Blockade in Tumors with Mismatch-repair Deficiency, The New England Journal of Medicine,—NEJM—, 2015, pp. 2509-2520 vol. 372.
Snyder, et al., Genetic basis for clinical response to CTLA-4 blockade in melanoma, New England Journal of Medicine, 2014, pp. 2189-2199 vol. 371.
Wang et al., "Overexpression of AGGF1 is correlated with angiogenesis and poor prognosis of hepatocellular carcinoma", Medical Oncology, Mar. 22, 2015, vol. 32, No. 131, 9 pages.
Tian et al., "Identification of an angiogenic factor that when mutated causes susceptibility to Klippel-Trenaunay syndrome", Nature, Feb. 12, 2004, vol. 427, pp. 640-645.
Fritsch et al., "Personal neoantigen cancer vaccines: The momentum builds", OncoImmunology, Jun. 2014, vol. 3, 4 pages.
International Search Report and Written Opinion received for PCT Application Serial No. PCT/US2016/026798 dated Jul. 18, 2016, 14 pages.
First Examination report received for Australian Patent Application Serial No. 2016339035, dated Nov. 6, 2019, 04 pages.
Carter Paul, "Improving The Efficacy Of Antibody-Based Cancer Therapies," Nature Reviews, Cancer, Nov. 2001, vol. 1, pp. 118-129.
International Search Report and Written Opinion received for PCT Application Serial No. PCT/US2016/029244 dated Aug. 9, 2016, 15 pages.
Sykulevet al., "Evidence that a Single Peptide-MHC Complex on a Target Cell Can Elicit a Cytolytic T Cell Response", Immunity, Jun. 1, 1996, vol. 4, No. 6, pp. 565-571.
Boegel et al., "HLA typing from RNA-Seq sequence reads", Genome Medicine, 2012, vol. 4, No. 102, 12 pages.
Kim et al., "HLA Haplotyping from RNA-seq Data Using Hierarchical Read Weighting", PLoS One, Jun. 2013, vol. 8, No. 6, pp. 1-10.
First Office Action received for Canadian Patent Application Serial No. 2987730 dated Jul. 31, 2018, 06 pages.
Second Office Action received for Canadian Patent Application Serial No. 2987730 dated Feb. 25, 2019, 04 pages.
Haisma H.J, "Monoclonal antibodies and cancer: Studies on the use of monoclonal antibodies for imaging and therapy of cancer, with a special emphasis on ovarian carcinoma", Dec. 8, 1957, 175 pages.
Gubin et al., Tumor neoantigens: building a framework for, personalized cancer immunotherapy, The Journal of Clinical Investigation, Sep. 2015, vol. 125, No. 9, pp. 3413-3421.
Srivastava P.K, "Neoepitopes of Cancers: Looking Back, Looking Ahead", Cancer Immunology Research, Sep. 1, 2015, vol. 3, No. 9, pp. 969-977.
Monteiro J, "Cancer Immunotherapy Scores Again", Cell, Jan. 15, 2015, vol. 160, p. 7-9.
Hundal et al., "pVAC-Seq: A genome-guided in silico approach to identifying tumor neoantigens", Genome Medicine, Jan. 29, 2016, vol. 8, No. 11, p. 1-11.
Akkawi et al., "The human VG5Q gene 2 transcript is over-expressed in colorectal and bladder carcinomas", Gene Therapy Molecular Biology, 2006, vol. 10, pp. 173-178.
Wang et al., "Overexpression of AGGFI 2 is correlated with angiogenesis and poor prognosis of hepatocellular carcinoma", Med. Oncol., 2015,, vol. 32, No. 131, pp. 1-9.
Supplementary European Search report received for European Patent Application Serial No. 16777432 dated Aug. 29, 2018, 03 pages.
Rabizadeh et al., "Comprehensive genomic transcriptomic tumor-normal gene panel analysis for enhanced precision in patients with lung cancer", Oncotarget, Apr. 2018, vol. 9, No. 27, pp. 19223-19232.
Carreno et al., "Supplementary Materials for A dendritic cell vaccine increases the breadth and diversity of melanoma neoantigen-specific T cells", Science, May 15, 2015, vol. 348, No. 6236, pp. 34 pages.
Matsushita et al., "Cancer exome analysis reveals a T-cell-dependent mechanism of cancer immunoediting", Nature, Feb. 16, 2012, vol. 482, 7 pages.
Reuschenbach et al., "A multiplex method for the detection of serum antibodies against in silica-predicted tumor antigens", Cancer Immunol Immunother, Aug. 2014, vol. 63, pp. 1251-1259.
Extended European Search report received for European Patent Application Serial No. 16784102.2 dated Apr. 5, 2019, 13 pages.
Liosa et al., "The vigorous immune microenvironment of microsatellite instable colon cancer is balanced by multiple counter-inhibitory checkpoints", Cancer Discovery, Jan. 2015, vol. 5, pp. 43-51.
First Office Action received for Japanese Patent Application Serial No. 2018519039 dated Nov. 12, 2019, 08 pages (Including English Translation).
International Preliminary Report on Patentability received for PCT Application Serial No. PCT/US2016026798 dated Oct. 10, 2017, 01 pages.
Herbst et al., "Predictive correlates of response to the anti-PD-L1 antibody MPDL3280A in cancer patients", Nature, Nov. 27, 2014, vol. 515, pp. 1-18.
First Office Action received for Russian Patent Application Serial No. 2017145136/10(077299) dated Sep. 13, 2019, 14 pages (Including English Translation).
Extended European Search report received for European Patent Application Serial No. 16777432.2 dated Nov. 30, 2018, 11 pages.
Non-Final office Action Received for U.S. Appl. No. 15/565,203, dated Jun. 18, 2019, 17 pages.
International Preliminary Report on Patentability Chapter II received for PCT Application Serial No. PCT/US2016/029244 dated Aug. 22, 2017, 18 pages.
Carreno et al., "A dendritic cell vaccine increases the breadth and diversity of melanoma neoantigen-specific T cells", Science, 2018, vol. 348, No. 6236, pp. 8 pages.
International Search Report and Written Opinion received for PCT Application Serial No. PCT/US2016/056692 dated Jan. 11, 2017, 13 pages.

(56) References Cited

OTHER PUBLICATIONS

First Examination report received for Australian Patent Application Serial No. 2016253145, dated Jan. 17, 2020, 05 pages.
Communication Pursuant to rule 164(1) EPC received in European Patent Application Serial No. 16784102.2, dated Jan. 3, 2019, 1 page.
International Preliminary Report received for PCT Application Serial No. PCT/US2016/056692 dated Jan. 9, 2018, 15 pages.
Office Action received for Israeli Patent Application Serial No. 258679 dated Apr. 8, 2021, 3 pages.
Second Examination report received for Australian Patent Application Serial No. 2016339035 dated Jun. 9, 2020, 03 pages.

* cited by examiner

SYSTEMS, COMPOSITIONS, AND METHODS FOR DISCOVERY OF MSI AND NEOEPITOPES THAT PREDICT SENSITIVITY TO CHECKPOINT INHIBITORS

This application claims priority to US provisional application with the Ser. No. 62/240,494, which was filed Oct. 12, 2015, and which is incorporated by reference herein.

FIELD OF THE INVENTION

The field of the invention is computational analysis of omics data to predict treatment options, especially as it relates to predicting a positive treatment response of a tumor to one or more checkpoint inhibitors.

BACKGROUND OF THE INVENTION

The background description includes information that may be useful in understanding the present invention. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Cancer immunotherapies have led to remarkable responses in some patients, however, many patients failed to respond, despite having the apparent same type of cancer as compared with immunotherapy responders. One possible explanation for such failure is that various effector cells of the immune system can be blocked by compounds (checkpoint inhibitors) that interact with one or more inhibitory regulatory pathways. Notably, some tumor cells can make use of the inhibitory regulatory pathways to so evade detection and destruction by the immune system. Among other components, PD-1 and CTLA-4 are the most studied receptors that are involved with inhibition of immune responses and specific drugs have now become available that block activation of these receptors. For example, antibodies directed to PD-1 (e.g., nivolumab and pembrolizumab) and CTLA4 (e.g., ipilimumab) have yielded significant clinical responses in some cases of melanoma, renal cell carcinoma, non-small cell lung cancer, and various other tumor types. Unfortunately, not all types of cancers respond equally well to treatment with checkpoint inhibitors. Moreover, even within the same type of cancer, positive response predictability for checkpoint inhibitors has been elusive.

In addition, loss of mismatch repair (MMR) often results in drug resistance directly by impairing the ability of the cell to detect DNA damage and activate apoptosis, and indirectly by increasing the mutation rate throughout the genome. For example, MMR-deficient cells have been reported to be resistant to various methylating/alkylating agents, certain platinum-containing drugs, antimetabolites, and topoisomerase II inhibitors. Moreover, MMR deficient cells have an increased mutation rate, which is often expressed as microsatellite instability (MSI). As these cells are often less sensitive to conventional drug treatment, immunotherapy would be desirable. However, efficacy of immunotherapy for MSI tumors is unpredictable as is treatment of MSI tumors with checkpoint inhibitors.

Thus, it would be desirable to have a prognostic tool that would help assess efficacy of treatment of a cancer with checkpoint inhibitors, alone or in combination with treatment that targets patient- and cancer-specific neoepitopes.

SUMMARY OF THE INVENTION

The inventive subject matter is directed to various devices, systems, and methods for predicting treatment response of a tumor to a checkpoint inhibitor. In especially preferred aspects, presence and quantity (and patterns) of HLA-matched neoepitopes are then used as proxy indicators for likely treatment success with checkpoint inhibitors.

In one aspect of the inventive subject matter, the inventors contemplate a method of improving treatment of a cancer using immunotherapy that includes a step of obtaining from a patient omics data from a tumor tissue and a matched normal tissue, and another step of using the omics data to determine a plurality of missense based patient- and tumor-specific neoepitopes. In a further step, the neoepitopes are then filtered and quantified to obtain HLA-matched neoepitopes. A checkpoint inhibitor (e.g., CTLA-4 inhibitor or PD-1 inhibitor) is then administered to the patient when it is determined that the quantity of HLA-matched neoepitopes has exceeded a predetermined threshold quantity.

Most typically, the step of filtering the neoepitopes is performed for each of the neoepitopes using a plurality of distinct individual neoepitope sequences (e.g., each having a length of between 7 and 20 amino acids) in which a changed amino acid has a distinct position within the neoepitope sequence. It is also contemplated that the step of filtering may further include a step of filtering by an a priori known molecular variation, such as a single nucleotide polymorphism, a short deletion and insertion polymorphism, a microsatellite marker, a short tandem repeat, a heterozygous sequence, a multinucleotide polymorphism, or a named variant. In further contemplated aspects, the step of filtering may also include a determination of affinity of the neoepitopes to at least one MHC Class I sub-type and/or to at least one MHC Class II sub-type of the patient, and may also include a determination of the expression level of the neoepitope.

While not limiting to the inventive subject matter, it is contemplated that the HLA-matched neoepitopes will have an affinity of equal or less than 150 nM to at least one MHC Class I sub-type and/or to at least one MHC Class II sub-type of the patient. For example, it is contemplated that the step of quantifying the HLA-matched neoepitopes may include a quantification of the affinity of the neoepitopes to at least one MHC Class I sub-type or to at least one MHC Class II sub-type of the patient (e.g., equal or less than 500 nM, or equal or less than 250 nM, or equal or less than 150 nM, or equal or less than 50 nM), and a determination of the total number of HLA-matched neoepitopes (e.g., at least 50, or at least 100, or at least 200, or at least 300, etc.).

In addition, it is contemplated that such methods may further comprise a step of filtering the HLA-matched neoepitopes by a mutation signature (e.g., signature characteristic for UV-induced DNA damage or smoking-induced DNA damage). Where desired, it is also contemplated that the methods presented herein may further include a step of using the omics data to detect microsatellite instability (MSI) and/or defective mismatch repair (MMR) in the diseased tissue.

Therefore, and viewed from a different perspective, the inventors also contemplate a method of predicting positive treatment response of a tumor to a checkpoint inhibitor. Such method will typically include a step of obtaining from a patient omics data from a tumor tissue and a matched normal tissue, and using the omics data to determine a plurality of missense based patient- and tumor-specific neoepitopes. In a further step, the neoepitopes are filtered and quantified to obtain HLA-matched neoepitopes. In still another step, it is determined —upon ascertaining that the quantity of HLA-matched neoepitopes has exceeded a predetermined threshold quantity —that the tumor is responsive to treatment with the checkpoint inhibitor.

Similarly, the inventors also contemplate method of predicting positive treatment response of a tumor to a checkpoint inhibitor, in which omics data from a tumor tissue and a matched normal tissue are obtained from a patient, and the omics data are then used to determine a plurality of missense based patient- and tumor-specific neoepitopes. In another step, the neoepitopes are filtered to obtain HLA-matched neoepitopes, and the HLA-matched neoepitopes are quantified. In a further step, a mutation signature is determined for the quantified HLA-matched neoepitopes, and the quantity of neoepitopes and the mutation signature are then employed as determinants for positive treatment response of the tumor to the checkpoint inhibitor.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
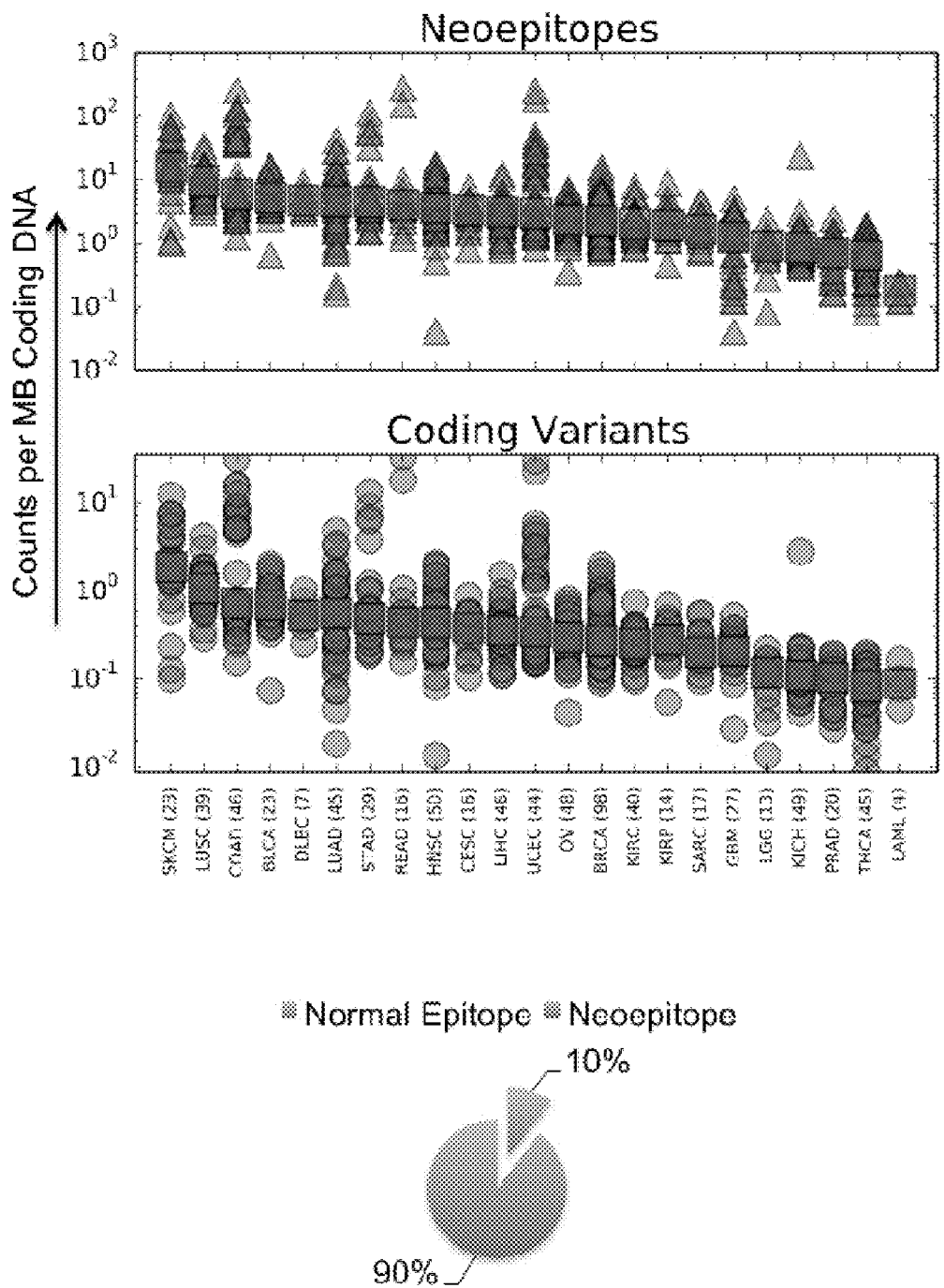
FIG. 1 is an exemplary graphical representation of neoepitope frequency and coding variant frequency across various cancers, as well as a graphical representation of frequency of unique neoepitopes across various cancers.

The inventors have now discovered that HLA-matched patient- and cancer-specific neoepitopes can be used as proxy indicators for likely treatment success of a tumor with one or more checkpoint inhibitors where the number of such neoepitopes is above a threshold level. Such relatively large numbers of the expressed neoepitopes may be due to or associated with various causes, including MMR and/or MSI. Additionally, the inventors also discovered that the patient- and cancer-specific neoepitopes could be indicative of likely treatment success where the neoepitopes were associated with a particular mutation pattern (e.g., UV-induced DNA damage, or smoking-induced DNA damage) that can give rise to unique and tumor specific antigens.

Neoepitopes can be characterized as expressed random mutations in tumor cells that created unique and tumor specific antigens. Therefore, viewed from a different perspective, neoepitopes may be identified by considering the type (e.g., deletion, insertion, transversion, transition, translocation) and impact of the mutation (e.g., non-sense, missense, frame shift, etc.), which may as such serve as a first content filter through which silent and other non-relevant (e.g., non-expressed) mutations are eliminated. It should further be appreciated that neoepitope sequences can be defined as sequence stretches with relatively short length (e.g., 7-11 mers) wherein such stretches will include the change(s) in the amino acid sequences. Most typically, the changed amino acid will be at or near the central amino acid position. For example, a typical neoepitope may have the structure of $A_4$-N-$A_4$, or $A_3$-N-$A_5$, or $A_2$-N-$A_7$, or $A_5$-N-$A_3$, or $A_7$-N-$A_2$, where A is a proteinogenic amino acid and N is a changed amino acid (relative to wild type or relative to matched normal). For example, neoepitope sequences as contemplated herein include sequence stretches with relatively short length (e.g., 5-30 mers, more typically 7-11 mers, or 12-25 mers) wherein such stretches include the change(s) in the amino acid sequences.

Thus, it should be appreciated that a single amino acid change may be presented in numerous neoepitope sequences that include the changed amino acid, depending on the position of the changed amino acid. Advantageously, such sequence variability allows for multiple choices of neoepitopes and so increases the number of potentially useful targets that can then be selected on the basis of one or more desirable traits (e.g., highest affinity to a patient HLA-type, highest structural stability, etc.). Most typically, neoepitopes will be calculated to have a length of between 2-50 amino acids, more typically between 5-30 amino acids, and most typically between 9-15 amino acids, with a changed amino acid preferably centrally located or otherwise situated in a manner that improves its binding to MHC. For example, where the epitope is to be presented by the MHC—I complex, a typical neoepitope length will be about 8-11 amino acids, while the typical neoepitope length for presentation via MHC-II complex will have a length of about 13-17 amino acids. As will be readily appreciated, since the position of the changed amino acid in the neoepitope may be other than central, the actual peptide sequence and with that actual topology of the neoepitope may vary considerably.

Of course, it should be appreciated that the identification or discovery of neoepitopes may start with a variety of biological materials, including fresh biopsies, frozen or otherwise preserved tissue or cell samples, circulating tumor cells, exosomes, various body fluids (and especially blood), etc. Therefore, suitable methods of omics analysis include nucleic acid sequencing, and particularly NGS methods operating on DNA (e.g., Illumina sequencing, ion torrent sequencing, 454 pyrosequencing, nanopore sequencing, etc.), RNA sequencing (e.g., RNAseq, reverse transcription based sequencing, etc.), and protein sequencing or mass spectroscopy based sequencing (e.g., SRM, MRM, CRM, etc.).

As such, and particularly for nucleic acid based sequencing, it should be particularly recognized that high-throughput genome sequencing of a tumor tissue will allow for rapid identification of neoepitopes. However, it must be appreciated that where the so obtained sequence information is compared against a standard reference, the normally occurring inter-patient variation (e.g., due to SNPs, short indels, different number of repeats, etc.) as well as heterozygosity will result in a relatively large number of potential false positive neoepitopes. Notably, such inaccuracies can be eliminated where a tumor sample of a patient is compared against a matched normal (i.e., non-tumor) sample of the same patient.

In one especially preferred aspect of the inventive subject matter, DNA analysis is performed by whole genome sequencing and/or exome sequencing (typically at a coverage depth of at least 10×, more typically at least 20×) of both tumor and matched normal sample. Alternatively, DNA data may also be provided from an already established sequence record (e.g., SAM, BAM, FASTA, FASTQ, or VCF file) from a prior sequence determination. Therefore, data sets may include unprocessed or processed data sets, and exemplary data sets include those having BAMBAM format, SAMBAM format, FASTQ format, or FASTA format. However, it is especially preferred that the data sets are provided in BAMBAM format or as BAMBAM diff objects (see e.g., US2012/0059670A1 and US2012/0066001A1). Moreover, it should be noted that the data sets are reflective of a tumor and a matched normal sample of the same patient to so obtain patient and tumor specific information. Thus, genetic germ line alterations not giving rise to the tumor (e.g., silent mutation, SNP, etc.) can be excluded. Of course, it should be recognized that the tumor sample may be from an initial tumor, from the tumor upon start of treatment, from a recurrent tumor or metastatic site, etc. In most cases, the matched normal sample of the patient may be blood, or non-diseased tissue from the same tissue type as the tumor.

Likewise, the computational analysis of the sequence data may be performed in numerous manners. In most preferred methods, however, analysis is performed in silico by location-guided synchronous alignment of tumor and normal samples as, for example, disclosed in US 2012/0059670A1 and US 2012/0066001A1 using BAM files and BAM servers. Such analysis advantageously reduces false positive neoepitopes and significantly reduces demands on memory and computational resources.

It should be noted that any language directed to a computer should be read to include any suitable combination of computing devices, including servers, interfaces, systems, databases, agents, peers, engines, controllers, or other types of computing devices operating individually or collectively. One should appreciate the computing devices comprise a processor configured to execute software instructions stored on a tangible, non-transitory computer readable storage medium (e.g., hard drive, solid state drive, RAM, flash, ROM, etc.). The software instructions preferably configure the computing device to provide the roles, responsibilities, or other functionality as discussed below with respect to the disclosed apparatus. Further, the disclosed technologies can be embodied as a computer program product that includes a non-transitory computer readable medium storing the software instructions that causes a processor to execute the disclosed steps associated with implementations of computer-based algorithms, processes, methods, or other instructions. In especially preferred embodiments, the various servers, systems, databases, or interfaces exchange data using standardized protocols or algorithms, possibly based on HTTP, HTTPS, AES, public-private key exchanges, web service APIs, known financial transaction protocols, or other electronic information exchanging methods. Data exchanges among devices can be conducted over a packet-switched network, the Internet, LAN, WAN, VPN, or other type of packet switched network; a circuit switched network; cell switched network; or other type of network.

Viewed from a different perspective, a patient- and cancer-specific in silico collection of sequences can be established that have a predetermined length of between 5 and 25 amino acids and include at least one changed amino acid. Such collection will typically include for each changed amino acid at least two, at least three, at least four, at least five, or at least six members in which the position of the changed amino acid is not identical. Such collection can then be used for further filtering (e.g., by sub-cellular location, transcription/expression level, MHC—I and/or II affinity, etc.) as is described in more detail below.

For example, and using synchronous location guided analysis to tumor and matched normal sequence data, the inventors previously identified various cancer neoepitopes from a variety of cancers and patients, including the following cancer types: BLCA, BRCA, CESC, COAD, DLBC, GBM, HNSC, KICH, KIRC, KIRP, LAML, LGG, LIHC, LUAD, LUSC, OV, PRAD, READ, SARC, SKCM, STAD, THCA, and UCEC. All neoepitope data can be found in International application PCT/US16/29244, incorporated by reference herein.

Depending on the type and stage of the cancer, it should be noted that not all of the identified neoepitopes will necessarily lead to a therapeutically equally effective reaction in a patient when checkpoint inhibitors are given to a patient. Indeed, it is well known in the art that only a fraction of neoepitopes will generate an immune response. To increase likelihood of a therapeutically desirable response, the neoepitopes can be further filtered. Of course, it should be appreciated that downstream analysis need not take into account silent mutations for the purpose of the methods presented herein. However, preferred mutation analyses will provide in addition to the type of mutation (e.g., deletion, insertion, transversion, transition, translocation) also information of the impact of the mutation (e.g., non-sense, missense, etc.) and may as such serve as a first content filter through which silent mutations are eliminated. For example, neoepitopes can be selected for further consideration where the mutation is a frame-shift, non-sense, and/or missense mutation.

In a further filtering approach, neoepitopes may also be subject to detailed analysis for sub-cellular location parameters. For example, neoepitope sequences may be selected for further consideration if the neoepitopes are identified as having a membrane associated location (e.g., are located at the outside of a cell membrane of a cell) and/or if an in silico structural calculation confirms that the neoepitope is likely to be solvent exposed, or presents a structurally stable epitope (e.g., *J Exp Med* 2014), etc.

With respect to filtering neoepitopes, it is generally contemplated that neoepitopes are especially suitable for use herein where omics (or other) analysis reveals that the neoepitope is actually expressed. Identification of expression and expression level of a neoepitope can be performed in all manners known in the art and preferred methods include quantitative RNA (hnRNA or mRNA) analysis and/or quantitative proteomics analysis. Most typically, the threshold level for inclusion of neoepitopes will be an expression level of at least 20%, at least 30%, at least 40%, or at least 50% of expression level of the corresponding matched normal sequence, thus ensuring that the (neo) epitope is at least potentially 'visible' to the immune system. Consequently, it is generally preferred that the omics analysis also includes an analysis of gene expression (transcriptomic analysis) to so help identify the level of expression for the gene with a mutation.

There are numerous methods of transcriptomic analysis known in the art, and all of the known methods are deemed suitable for use herein. For example, preferred materials include mRNA and primary transcripts (hnRNA), and RNA sequence information may be obtained from reverse transcribed polyA$^+$-RNA, which is in turn obtained from a tumor sample and a matched normal (healthy) sample of the same patient. Likewise, it should be noted that while polyA$^+$-RNA is typically preferred as a representation of the transcriptome, other forms of RNA (hn-RNA, non-polyadenylated RNA, siRNA, miRNA, etc.) are also deemed suitable for use herein. Preferred methods include quantitative RNA (hnRNA or mRNA) analysis and/or quantitative proteomics analysis, especially including RNAseq. In other aspects, RNA quantification and sequencing is performed using RNA-seq, qPCR and/or rtPCR based methods, although various alternative methods (e.g., solid phase hybridization-based methods) are also deemed suitable. Viewed from another perspective, transcriptomic analysis may be suitable (alone or in combination with genomic analysis) to identify and quantify genes having a cancer- and patient-specific mutation.

Similarly, proteomics analysis can be performed in numerous manners to ascertain actual translation of the RNA of the neoepitope, and all known manners of proteomics analysis are contemplated herein. However, particularly preferred proteomics methods include antibody-based methods and mass spectroscopic methods. Moreover, it should be noted that the proteomics analysis may not only provide qualitative or quantitative information about the protein per se, but may also include protein activity data where the protein has catalytic or other functional activity. One exemplary technique for conducting proteomic assays is described in U.S. Pat. No. 7,473,532, incorporated by reference herein. Further suitable methods of identification and even quantification of protein expression include various mass spectroscopic analyses (e.g., selective reaction monitoring (SRM), multiple reaction monitoring (MRM), and consecutive reaction monitoring (CRM)).

In yet another aspect of filtering, the neoepitopes may be compared against a database that contains known human sequences (e.g., of the patient or a collection of patients) to so avoid use of a human-identical sequence. Moreover, filtering may also include removal of neoepitope sequences that are due to SNPs in the patient where the SNPs are present in both the tumor and the matched normal sequence. For example, dbSNP (The Single Nucleotide Polymorphism Database) is a free public archive for genetic variation within and across different species developed and hosted by the National Center for Biotechnology Information (NCBI) in collaboration with the National Human Genome Research Institute (NHGRI). Although the name of the database implies a collection of one class of polymorphisms only (single nucleotide polymorphisms (SNPs)), it in fact contains a relatively wide range of molecular variation: (1) SNPs, (2) short deletion and insertion polymorphisms (indels/DIPs), (3) microsatellite markers or short tandem repeats (STRs), (4) multinucleotide polymorphisms (MNPs), (5) heterozygous sequences, and (6) named variants. The dbSNP accepts apparently neutral polymorphisms, polymorphisms corresponding to known phenotypes, and regions of no variation.

Using such database and other filtering options as described above, the patient and tumor specific neoepitopes may be filtered to remove those known sequences, yielding a sequence set with a plurality of neoepitope sequences having substantially reduced false positives.

Nevertheless, despite filtering, it should be recognized that not all neoepitopes will be visible to the immune system as the neoepitopes also need to be presented on the MHC complex of the patient. Indeed, only a fraction of the neoepitopes will have sufficient affinity for presentation, and the large diversity of MHC complexes will preclude use of most, if not all, common neoepitopes. Consequently, in the context of immune therapy it should thus be readily apparent that neoepitopes will be more likely effective where the neoepitopes are bound to and presented by the MHC complexes. Viewed from another perspective, treatment success with checkpoint inhibitors requires multiple neoepitopes to be presented via the MHC complex in which the neoepitope must have a minimum affinity to the patient's HLA-type. Consequently, it should be appreciated that effective binding and presentation is a combined function of the sequence of the neoepitope and the particular HLA-type of a patient. Most typically, the HLA-type determination includes at least three MHC—I sub-types (e.g., HLA-A, HLA-B, HLA-C) and at least three MHC-II sub-types (e.g., HLA-DP, HLA-DQ, HLA-DR), preferably with each subtype being determined to at least 4-digit depth. However, greater depth (e.g., 6 digit, 8 digit) is also contemplated herein.

Once the HLA-type of the patient is ascertained (using known chemistry or in silico determination), a structural solution for the HLA-type is calculated or obtained from a database, which is then used in a docking model in silico to determine binding affinity of the (typically filtered) neoepitope to the HLA structural solution. As will be further discussed below, suitable systems for determination of binding affinities include the NetMHC platform (see e.g., Nucleic Acids Res. 2008 Jul. 1; 36(Web Server issue): W509-W512.). Neoepitopes with high affinity (e.g., less than 100 nM, less than 75 nM, less than 50 nM) for a previously determined HLA-type are then selected for therapy creation, along with the knowledge of the MHC—I/II subtype.

HLA determination can be performed using various methods in wet-chemistry that are well known in the art, and all of these methods are deemed suitable for use herein. However, in especially preferred methods, the HLA-type can also be predicted from omics data in silico using a reference sequence containing most or all of the known and/or common HLA-types as is shown in more detail below.

For example, in one preferred method according to the inventive subject matter, a relatively large number of patient sequence reads mapping to chromosome 6p21.3 (or any other location near/at which HLA alleles are found) is provided by a database or sequencing machine. Most typically the sequence reads will have a length of about 100-300 bases and comprise metadata, including read quality, alignment information, orientation, location, etc. For example, suitable formats include SAM, BAM, FASTA, GAR, etc. While not limiting to the inventive subject matter, it is generally preferred that the patient sequence reads provide a depth of coverage of at least 5×, more typically at least 10×, even more typically at least 20×, and most typically at least 30×.

In addition to the patient sequence reads, contemplated methods further employ one or more reference sequences that include a plurality of sequences of known and distinct HLA alleles. For example, a typical reference sequence may be a synthetic (without corresponding human or other mammalian counterpart) sequence that includes sequence segments of at least one HLA-type with multiple HLA-alleles of that HLA-type. For example, suitable reference sequences include a collection of known genomic sequences for at least 50 different alleles of HLA-A. Alternatively, or additionally, the reference sequence may also include a collection of known RNA sequences for at least 50 different alleles of HLA-A. Of course, and as further discussed in more detail below, the reference sequence is not limited to 50 alleles of HLA-A, but may have alternative composition with respect to HLA-type and number/composition of alleles. Most typically, the reference sequence will be in a computer readable format and will be provided from a database or other data storage device. For example, suitable reference sequence formats include FASTA, FASTQ, EMBL, GCG, or GenBank format, and may be directly obtained or built from data of a public data repository (e.g., IMGT, the International ImMunoGeneTics information system, or The Allele Frequency Net Database, EUROSTAM, allelefrequencies.net). Alternatively, the reference sequence may also be built from individual known HLA-alleles based on one or more predetermined criteria such as allele frequency, ethnic allele distribution, common or rare allele types, etc.

Using the reference sequence, the patient sequence reads can now be threaded through a de Bruijn graph to identify the alleles with the best fit. In this context, it should be noted that each individual carries two alleles for each HLA-type, and that these alleles may be very similar, or in some cases even identical. Such high degree of similarity poses a significant problem for traditional alignment schemes. The inventor has now discovered that the HLA alleles, and even very closely related alleles can be resolved using an approach in which the de Bruijn graph is constructed by decomposing a sequence read into relatively small k-mers (typically having a length of between 10-20 bases), and by implementing a weighted vote process in which each patient sequence read provides a vote ("quantitative read support") for each of the alleles on the basis of k-mers of that sequence read that match the sequence of the allele. The cumulatively highest vote for an allele then indicates the most likely predicted HLA allele. In addition, it is generally preferred that each fragment that is a match to the allele is also used to calculate the overall coverage and depth of coverage for that allele.

Scoring may further be improved or refined as needed, especially where many of the top hits are similar (e.g., where a significant portion of their score comes from a highly shared set of k-mers). For example, score refinement may include a weighting scheme in which alleles that are substantially similar (e.g., >99%, or other predetermined value) to the current top hit are removed from future consideration. Counts for k-mers used by the current top hit are then re-weighted by a factor (e.g., 0.5), and the scores for each HLA allele are recalculated by summing these weighted counts. This selection process is repeated to find a new top hit. The accuracy of the method can be even further improved using RNA sequence data that allows identification of the alleles expressed by a tumor, which may sometimes be just 1 of the 2 alleles present in the DNA. In further advantageous aspects of contemplated systems and methods, DNA or RNA, or a combination of both DNA and RNA can be processed to make HLA predictions that are highly accurate and can be derived from tumor or blood DNA or RNA. Further aspects, suitable methods and considerations for high-accuracy in silico HLA typing are described in International PCT/US16/48768, incorporated by reference herein.

Once patient and tumor specific neoepitopes and HLA-type are identified, further computational analysis can be performed by docking neoepitopes to the HLA and determining best binders (e.g., lowest $K_D$, for example, less than 500 nM, or less than 250 nM, or less than 150 nM, or less than 50 nM), for example, using NetMHC. It should be appreciated that such approach will not only identify specific neoepitopes that are genuine to the patient and tumor, but also those neoepitopes that are most likely to be presented on a cell and as such most likely to elicit an immune response with therapeutic effect. Of course, it should also be appreciated that thusly identified HLA-matched neoepitopes can be biochemically validated in vitro prior to inclusion of the nucleic acid encoding the epitope as payload into the virus as is further discussed below.

Of course, it should be appreciated that matching of the patient's HLA-type to the patient- and cancer-specific neoepitope can be done using systems other than NetMHC, and suitable systems include NetMHC II, NetMHCpan, IEDB Analysis Resource (URL immuneepitope.org), RankPep, PREDEP, SVMHC, Epipredict, HLABinding, and others (see e.g., *J Immunol Methods* 2011; 374:1-4). In calculating the highest affinity, it should be noted that the collection of neoepitope sequences in which the position of the altered amino acid is moved (supra) can be used. Alternatively, or additionally, modifications to the neoepitopes may be implemented by adding N- and/or C-terminal modifications to further increase binding of the expressed neoepitope to the patient's HLA-type. Thus, neoepitopes may be native as identified or further modified to better match a particular HLA-type. Moreover, where desired, binding of corresponding wildtype sequences (i.e., neoepitope sequence without amino acid change) can be calculated to ensure high differential affinities. For example, especially preferred high differential affinities in MHC binding between the neoepitope and its corresponding wildtype sequence are at least 2-fold, at least 5-fold, at least 10-fold, at least 100-fold, at least 500-fold, at least 1000-fold, etc.).

Based on further observations (data not shown), the inventors contemplate that omics data of the patient may also be analyzed (preferably using synchronous location-guided alignment of exome or whole genome sequencing) to identify a type or pattern of particular mutations, and that such pattern (especially in combination with a minimum number of neoepitopes as described above) may be further indicative of likely treatment success with a checkpoint inhibitor. For example, where neoepitopes are associated with a mutational pattern typical for UV damage (e.g., tandem CC>TT/GG>AA mutations) and where more than 50, or 70, or 100 HLA-matched patient- and cancer-specific neoepitopes are present, successful treatment with a checkpoint inhibitor may be more likely than in cases without the mutational pattern and/or where less HLA-matched patient- and cancer-specific neoepitopes are present. Similarly, where neoepitopes are associated with a mutational pattern typical for smoking-induced DNA damage (e.g., high frequency of G>T mutation) and where more than 50, or 70, or 100 neoepitopes are present, successful treatment with a checkpoint inhibitor may be more likely than in cases without the mutational pattern and/or where less HLA-matched patient- and cancer-specific neoepitopes are present.

Additionally, it is contemplated that the increased number of neoepitopes may be due to various underlying conditions or phenomena. For example, it is postulated that a higher number of neoepitopes may be triggered by a defective or abnormal function of the MMR (DNA mismatch repair)

system in the cell, which may lead to multiple strand breaks and higher mutation rate and potentially a higher count of HLA-matched patient- and cancer-specific neoepitopes, which may also be observed as MSI (microsatellite instability). Thus, it is also contemplated that observations of MMR and/or MSI from whole genome and/or exome sequencing may be used as a proxy indicator for an increased number of HLA-matched patient- and cancer-specific neoepitopes. MMR and/or MSI are preferably identified against matched normal using known omics analysis algorithms and data visualization (for example using circle plot diagrams).

Once neoepitopes have been appropriately filtered using one or more of the methods as described above, so filtered neoepitopes can be quantified/counted. As will be readily appreciated, therapeutically effective treatment of cancer with immune checkpoint inhibitors is dependent on the presence of expressed and presented neoepitopes. While not wishing to be bound by any particular theory or hypothesis, the inventors generally contemplate that only a fraction of expressed and presented neoepitopes will lead to a therapeutic response, and that a tumor may have a heterogeneous population of cancer cells, each population likely with respective individual neoepitopes. Therefore, the inventors contemplate that treatment of cancers with immune checkpoint inhibitors will require a minimum/threshold quantity of HLA-matched patient- and cancer-specific neoepitopes. Based on retrospective analysis of various cancer data and as further discussed in more detail below, the inventors therefore contemplate that checkpoint inhibitors should be administered to a patient when the quantity of HLA-matched patient- and cancer-specific neoepitopes have exceeded a predetermined threshold quantity. Most typically, the predetermined threshold quantity is at least 50 HLA-matched patient- and cancer-specific neoepitopes, or at least 100 HLA-matched patient- and cancer-specific neoepitopes, or at least 150 HLA-matched patient- and cancer-specific neoepitopes.

Viewed from a different perspective, it should be appreciated that diagnosis of a relatively high number of mutations in a cancer is per se not predictive of a therapeutic response in treatment of cancer with a checkpoint inhibitor as a large number of such mutations (a) may not result in a neoepitope, for example, due to a silent mutation, (b) may have a corresponding matched normal sequence and as such not present a neoepitope at all, (c) may not be expressed and as such not be visible to the immune system, (d) may not bind to the patient specific MHC-complexes and as such not be visible to the immune system. In contrast, contemplated systems and methods identify HLA-matched patient- and cancer-specific neoepitopes with high confidence. Conversely, it should be recognized that cancers with a relatively low mutation frequency may indeed be treatable in a patient where the patients mutations translate in a relatively high number of HLA-matched patient- and cancer-specific neoepitopes (e.g., at least 50, or 100, or 150, or 200, etc.).

With respect to suitable checkpoint inhibitors it is contemplated that all compounds and compositions that interfere with checkpoint signaling (e.g., CTLA-4 (CD152) or PD-1 (CD 279)) are deemed suitable for use herein. For example, particularly preferred checkpoint inhibitors include pembrolizumab, nivolumab, and ipilimumab. Most typically, checkpoint inhibitors will be administered following conventional protocol and as described in the prescription information. However, it should be noted that where the checkpoint inhibitors are peptides or proteins, such peptides and/or proteins can also be expressed in the patient from any suitable expression system (along or in combination with neoepitopers and/or co-stimulatory molecules). Moreover, as used herein, the term 'administering' with respect to a checkpoint inhibitor refers to direct administration (e.g., by a physician or other licensed medical professional) or indirect administration (e.g., causing or advising to administer) of the checkpoint inhibitor to a patient.

In still further contemplated aspects, a combination therapy may be suitable that uses checkpoint inhibitors together with one or more anticancer therapeutic agents. Among other agents, it is especially preferred that the tumor may be treated with a virus that is genetically modified with a nucleic acid construct that leads to expression of at least one of the identified neoepitopes to so potentiate immune response against the tumor. For example, suitable viruses include adenoviruses, adeno-associated viruses, alphaviruses, herpes viruses, lentiviruses, etc. However, adenoviruses are particularly preferred. Moreover, it is further preferred that the virus is a replication deficient and non-immunogenic virus, which is typically accomplished by targeted deletion of selected viral proteins (e.g., E1, E3 proteins). Such desirable properties may be further enhanced by deleting E2b gene function, and high titers of recombinant viruses can be achieved using genetically modified human 293 cells as has been recently reported (e.g., *J Virol.* 1998 February; 72(2): 926-933). Most typically, the desired nucleic acid sequences (for expression from virus infected cells) are under the control of appropriate regulatory elements well known in the art. Alternatively, immune therapy need not rely on a virus but may be effected with nucleic acid vaccination, or other recombinant vector that leads to the expression of the neoepitopes (e.g., as single peptides, tandem mini-gene, etc.)

Likewise, further immunotherapeutic agents other than viral expression vectors are also deemed suitable and include genetically engineered cells (and especially various immune competent cells) that express a chimeric antigen receptor, or a high affinity CD16 receptor. For example, contemplated immunotherapeutic agents include NK cells (e.g., aNK cells, haNK cels, or taNK cells, commercially available from NantKwest, 9920 Jefferson Blvd. Culver City, Calif. 90232) or genetically modified T-cells (e.g., expressing a T-cell receptor) or T-cells stimulated ex vivo with HLA-matched patient- and cancer-specific neoepitopes. Alternatively, the HLA-matched patient- and cancer-specific neoepitopes may also be administered as peptides, optionally bound to a carrier protein.

Examples

Data Sets: TCGA WGS and RNAseq data for various cancers as indicated below were downloaded from the University of California, Santa Cruz (UCSC) Cancer Genomics Hub (cghub.ucsc.edu/). TCGA samples were selected based on the availability of complete WGS data to aid with in-silico HLA typing. RNAseq data of corresponding samples were used when available.

Identification of tumor variants and neoepitopes: Single nucleotide variants (SNVs) and insertions/deletions (indels) were identified by location-guided synchronous alignment of tumor and normal samples using BAM files in a manner substantially as disclosed in US 2012/0059670A1 and US 2012/0066001A1. Since HLA-A alleles predominantly bind to 9-mer peptide fragments, the inventors focused on the identification of 9-mer neoepitopes. Neoepitopes were identified by creating all possible permutations of 9-mer amino acid strings derived from an identified SNV or indel (i.e., each 9-mer had the changed amino acid in a unique position). As a means to reduce possible off-target effects of a particular neoepitope, the inventors filtered all identified neoepitopes against all possible 9-mer peptide sequences created from every known human gene. In addition, the inventors also filtered for single nucleotide polymorphisms from dbSNP (ncbi.nlm.nih.gov/SNP/) to account for rare protein sequences that may have been missed within the sequencing data. Neoepitopes were further ranked by RNA expression as well as by allele frequency of the observed coding variant to offset issues arising from tumor heterogeneity.

HLA typing: HLA typing data were not available for TCGA samples; therefore, the inventors performed in-silico HLA typing using WGS, RNAseq data, and the HLA forest algorithm substantially as described in PCT/US16/48768. Briefly, the Burrows-Wheeler alignment algorithm was used to align sequencing reads to every different HLA allele within the IMGT/HLA database (ebi.ac.uk/ipd/imgt/hla/). Each alignment is given a score based on conservation of bases, with the read quality score taken into account. Each HLA allele will then have a sum of scores accounting for how well each read aligns to a certain HLA allele, and the allele with the highest score is selected as a primary allele typing. Secondary allele typing is then performed by removing reads that perfectly align to the primary allele typing, and subsequent reads are then rescored without alignments to the primary allele. Using this process, the inventors obtained typing results for HLA-A, HLA-B, HLA-C, and HLA-DRB1 for all samples to a level of at least 4 digits.

Neoepitope-HLA affinity determination: NetMHC 3.4 (cbs.dtu.dk/services/NetMHC-3.4/) was used to predict whether a neoepitope would bind to a specific HLA allele. To reduce the complexity space, the inventors chose to restrict binding analysis to HLA-A alleles, as they are the most well-characterized HLA alleles and have the best binding affinity models. Because the NetMHC 3.4 tool does not have models for every identified HLA-A allele, a HLA supertype was chosen for binding predictions if the patient's HLA-A typing was not available for use in NetMHC 3.4. Neoepitopes with predicted binding affinities <500 nM protein concentration were retained for further analysis. However, other more stringent binding criteria (<250 nM, or <150 nM, or <50 nM) are also deemed appropriate. *Homo sapiens*

Coding mutation and neoepitope load across cancer types: WGS data and corresponding RNAseq data, when available, were used to establish a baseline of potential neoepitopes and somatic coding variants per megabase of coding DNA for 750 patient samples across 23 cancer classifications as is shown in FIG. 1. Here, neoepitope and variant counts are shown for 750 patient samples across 23 cancer classifications within TCGA. Panel (a) illustrates neoepitope counts; Panel (b) illustrates variant counts. The y-axis shows counts per megabase of coding DNA (88 MB for human genome assembly (hg)19). The x-axis shows each cancer classification with the number of patient samples shown in parenthesis. Median sample counts are indicated by squares. Pane (c) indicates the percentage of neoepitopes and normal epitopes within all cancer types.

As can be readily taken from FIG. 1, mutational and neoepitope loads varied across different cancer types, with melanoma and squamous cell lung cancer having the highest neoepitope load and thyroid cancer and acute myeloid leukemia having the lowest neoepitope load. Filtering of presumptive neoepitopes against a database of known human sequences to remove potential off-target effects revealed that only 10% of identified neoepitopes map to a fragment of a known protein; therefore, most mutations generate a unique protein sequence. However, even though the fraction of unique neoepitopes is relatively high, expression and presentation cannot be presumed to occur. Indeed, as is further shown in more detail below, it should be recognized that the number of expressed and presented neoepitopes is dramatically lower than the number of neoepitopes identified by sequencing only.

Figure 2:
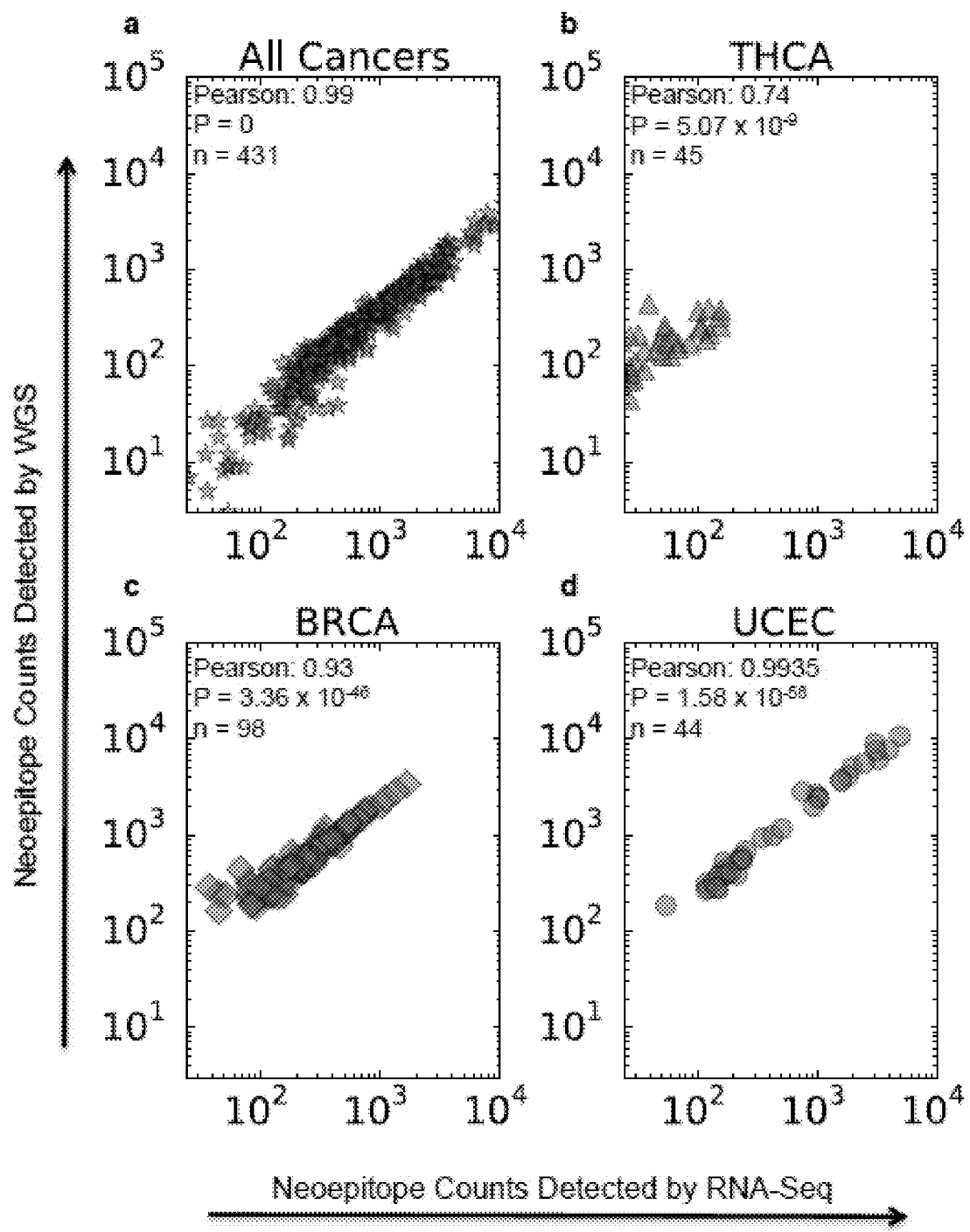
FIG. 2 is an exemplary graphical representation of neoepitope frequency and their expression into RNA in cancers.

Neoepitope mutational load and expression: Due to the length of epitopes presented by the MHC class I (MHC—I), a single mutation may nevertheless result in the expression of numerous distinct neoepitopes. Therefore, an individual patient's tumor containing hundreds of mutations will likely contain thousands of neoepitopes. Although many tumor mutations are likely to be passenger mutations and not responsible for cancer progression, they could potentially be exploited as targets for therapeutic intervention. RNAseq data were used to select for neoepitopes that are expressed within all cancer classifications combined, and also within cancer classifications that have different mutational loads: uterine corpus endometrial carcinoma, thyroid carcinoma, and breast invasive carcinoma. Most notably, the neoepitope counts identified by WGS correlated with neoepitope expression identified by RNAseq across a wide variety of cancers (Pearson's r=0.99 for all cancers combined) as can be seen in FIG. 2. Here, Panel (a) depicts all cancer, Panel (b) depicts thyroid carcinoma (THCA), Panel (c) depicts breast invasive carcinoma (BRCA), and Panel (d) depicts uterine corpus endometrial carcinoma (UCEC). The y-axis shows the raw counts of neoepitopes per sample as identified by WGS, and the x-axis shows raw counts of neoepitopes after filtering against expressed genes as determined by RNAseq. Pearson correlations, P-values, and sample numbers are shown on each graph. Cancers with a high neoepitope load generally had high neoepitope expression, regardless of the average mutational load.

Identification of neoepitopes in triple negative breast cancer: Triple-negative breast cancer (TNBC) is an aggressive cancer with limited treatment options and often very poor prognosis following progression after standard chemotherapy. The TCGA dataset contained WGS data and RNAseq data for 26 TNBC samples. The neoepitope counts in TNBC were identified using an iterative approach as follows: every possible neoepitope was predicted based on the coding variants identified by WGS; the number of neoepitopes was narrowed by selecting expressed neoepitopes identified by RNAseq; and the list was further refined by selecting neoepitopes predicted to bind to the specific alleles within a patient's HLA type. This selective pruning of neoepitopes yielded a list of high-quality neoepitopes, which were unique to each patient as shown in Table 1.

TABLE 1

| TCGA Barcode | HLA-A Typing | HUGO Gene Name | TPM | Neoepitope | Protein Change | Normal | Bound HLA-A Allele | Affinity for HLA-A |
|---|---|---|---|---|---|---|---|---|
| TCGA-E2-A14X-01A-11D-A10Y-09 | A*23:01, A*11:01 | NAA50 | 229.85 | PTDAHVLQK | p.A145T | PADAHVLQK | A*11:01 | 146 nM |

TABLE 1 -continued

| TCGA Barcode | HLA-A Typing | HUGO Gene Name | TPM | Neoepitope | Protein Change | Normal | Bound HLA-A Allele | Affinity for HLA-A |
|---|---|---|---|---|---|---|---|---|
| TCGA-E2-A1LL-01A-11D-A142-09 | A*02:01, A*02:01 | FBXO2 | 187.36 | LLLHVLAAL | p.R57H | LLLRVLAAL | A*02:01 | 18 nM |
| TCGA-AN-A0G0-01A-11D-A045-09 | A*11:01, A*11:01 | C1orf43 | 574.04 | TQSCYNYLY | p.N94T | NQSCYNYLY | A*11:01 | 225 nM |
| TCGA-A2-A0D2-01A-21D-A128-09 | A*03:01, A*32:01 | TBCD | 57.13 | TVVRWSVAK | p.A380V | TVVRWSAAK | A*03:01 | 119 nM |
| TCGA-A7-A26G-01A-21D-A167-09 | A*01:01, A*01:01 | PTEN | 41.3 | RTGVMKCAY | p.I135K | RTGVMICAY | A*01:01 | 480 nM |

Figure 3:
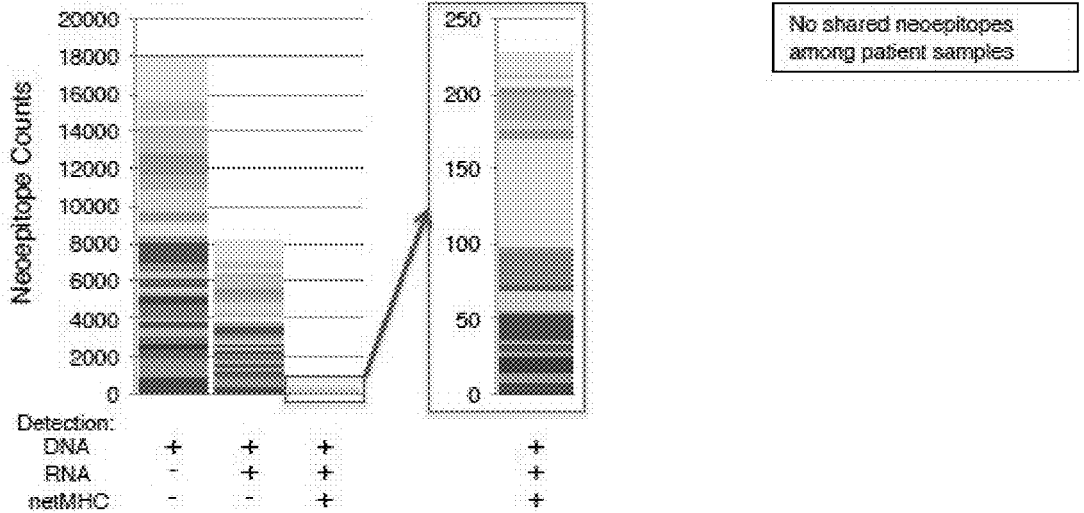
FIG. 3 is an exemplary graphical representation of the frequency for HLA-matched neoepitopes for various cancers.
Figure 3:
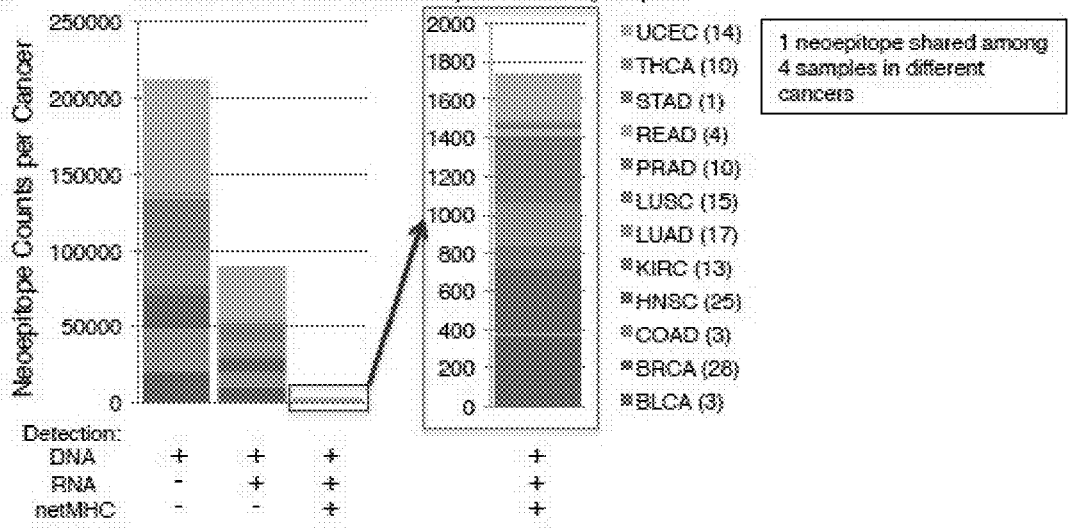
Figure 3:
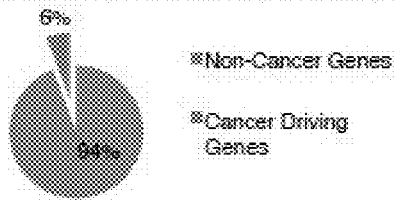

As is depicted in FIG. 3 (top panel, a) for all 26 patients, the numbers of predicted neoepitopes, expressed neoepitopes, and neoepitopes with affinity to each patient-specific HLA-A type were 17,925, 8184, and 228, respectively. Clearly, reliance on a high number of neoepitopes as determined by sequencing (and even sequencing and analysis of tumor versus matched normal) will not provide a meaningful predictor for responsiveness to treatment with checkpoint inhibitors. Likewise, further consideration of the expression will only moderately remove false positive results, while normalization of the results to actual HLA-binders will substantially increase the fraction of expressed and presented patient- and tumor-specific neoepitopes.

Identification of neoepitopes across cancer classifications: Since there were no shared neoepitopes among patients with TNBC, the inventors sought to determine whether any neoepitopes are shared among the other cancer classifications within the TCGA dataset. To ensure that common neoepitopes would also bind to the HLA complex, the inventors limited the analysis to samples containing the HLA-A*02:01 allele, which occurs in high frequencies across North America. Using the same iterative approach performed for TNBC, the inventors identified neoepitopes across 12 cancers that had complete WGS and RNAseq data and results are shown in FIG. 3 (bottom panel, b). Shading within each bar indicates a different patient sample.

Here, the numbers of predicted neoepitopes, expressed neoepitopes, and neoepitopes with affinity to HLA-A*02:01 were 211,285, 89,351, and 1,732, respectively. Correcting for different sample sizes, the average number of predicted neoepitopes, expressed neoepitopes, and neoepitopes with affinity to HLA-A*02:01 were 23,272, 9,619, and 138, respectively. Across this data, one neoepitope was identified that occurred in four different patient samples representing four different cancer types: bladder cancer, urothelial carcinoma, lung squamous cell carcinoma, lung adenocarcinoma, and breast invasive carcinoma. A number of neoepitopes were shared between pairs of patients representing two different cancer types (Table 2).

TABLE 2

| TCGA Barcode | HUGO Gene Name | Neoepitope | Protein Change | Normal | Cancer Type |
|---|---|---|---|---|---|
| TCGA-E2-A109-01A-11D-A10M-09, TCGA-CR-5249-01A-01D-2276-10, TCGA-BA-6872-01A-11D-A32X-10, TCGA-CN-6989-01A-11D-A32X-10 | SOS2 | YIHTHTFYV | p.T390I | YTHTHTFYV | HNSC, n = 3<br>BRCA, n = 1 |
| TCGA-EW-A115-01A-11D-A13L-09, TCGA-21-1082-01A-01D-1521-TCGA-GD-A2C5-01A-12D-A17V-08, TCGA-75-5147-01A-01D-1625-08 | USP8 | SQIWNLNPV | p.R763W | SQIRNLNPV | LUAD, n = 1<br>BLCA, n = 1<br>LUSC, n = 1<br>BRCA, n = 1 |
| TCGA-B6-AORT-01A-21D-A128-09, TCGA-AQ-A041-01A-02D-A128-09 | AKAP11 | SCMNPQTFK | p.K400T | SCMNPQKFK | BRCA, n = 2 |
| TCGA-55-7281-01A-11D-2036-08, TCGA-AO-A03L-01A-41D-A19H-09 | PCMTD1 | KLSLPESLK | p.P3425 | KLPLPESLK | LUAD, n = 1<br>BRCA, n = 1 |

TABLE 2 -continued

| TCGA Barcode | HUGO Gene Name | Neoepitope | Protein Change | Normal | Cancer Type |
|---|---|---|---|---|---|
| TCGA-EL-A3T0-01A-22D-A22D-08, TCGA-A8-A08L-01A-11D-A19H-09 | PKD1 | AMPSPEARV | p.T938M | ATPSPEARV | THCA, n = 1 BRCA, n = 1 |

Notably, initial neoepitope predictions based only on WGS identified several neoepitopes that recurred among TNBC patients (data not shown). After neoepitope-HLA binding analysis, all of the recurrent neoepitopes were eliminated due to differences in HLA alleles and binding potentials among patients. Even among 12 cancer classifications combined, recurrent neoepitopes were rare, with only one detected neoepitope shared among 4 patients with distinct cancer types, once more again highlighting the need for comprehensive molecular profiling. FIG. 3 (bottom pie chart, c) further illustrates that across all cancers, approximately 6% of neoepitopes occurred in cancer driver genes, which is in agreement with previous observations.

Certain tumors such as melanoma and lung cancer have a high mutational load with increased expression of somatic neoepitopes that should elicit antitumor responses and make these cancers more responsive to checkpoint inhibitors. On the other hand, cancers that have relatively low mutation/neoepitope load should be less likely to have an expressed/bound neoepitope and as such should be less responsive to therapy with checkpoint inhibitors. Unfortunately, such assumption is oversimplified and actual responsiveness to checkpoint inhibitor treatment will to a large degree depend on the patient and tumor specific match between tumor specific expressed neoepitopes and the patient specific affinity of the neoepitope to the HLA-type of the patient. For example, although the melanoma and lung cancer samples within TCGA had a high average mutational load, some individual samples had a low mutational load. Therefore, it should be appreciated that ordinary classification by disease type only will be over-inclusive, and as such subject patients to treatment that is not likely effective. The inventors also identified many individual tumor samples across a diverse array of cancer types that have high mutational burdens, potentially rendering patients sensitive to treatment with checkpoint inhibitors. Taken together the inventors' findings suggest that a detailed molecular analysis of a patient's tumor is needed to determine the potential benefit of checkpoint inhibitors outside of the approved indications for these agents. As a guiding principle, and in view of the data and contemplations provided above, analysis should be focused on HLA-matched (i.e., neoepitopes with high affinity to patient HLA-type, typically below 250 nM, or below 150 nM) patient- and cancer-specific neoepitopes that must be present above a threshold number (e.g., at least 50, more typically at least 100).

Figure 4:
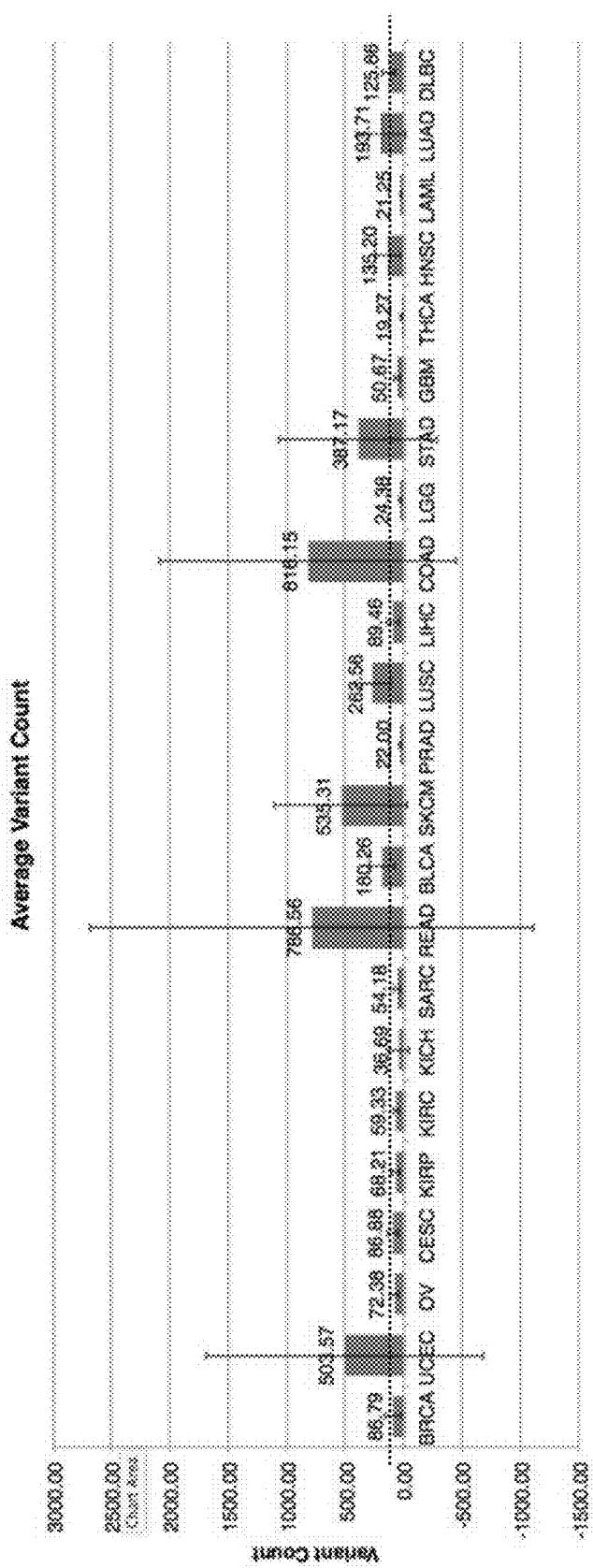
FIG. 4 is an exemplary graphical representation of the effect of various filtering processes for neoepitopes for a single cancer type (TNBC) and HLA-restricted neoepitopes for combined cancers. Also exemplarily shown is the location of neoepitopes with respect to cancer driving genes and non-cancer genes.

FIG. 4 exemplarily depicts the variant count for various cancer neoepitopes that were identified as described above. As is readily apparent, certain cancers have a relatively high number of neoepitopes, while other cancers have only moderate numbers of neoepitopes. Moreover, it should be noted that the variability of neoepitope occurrence within the same type of cancer is not homogenous. Indeed, some cancers have relatively low average number of neoepitopes, but high variability extending well above the predetermined threshold value of 100 (e.g., HNSC, LUAD; threshold shown in dashed line). Notably, cancers with neoepitope count above the threshold were shown to have a significantly higher likelihood to be responsive to treatment with a checkpoint inhibitor (e.g., UCEC, READ, BLCA, SKCM, LUSC, COAD, STAD). Furthermore, it was also observed that these cancers were also typically associated with MMR and/or MSI.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

SEQUENCE LISTING

<110>Nantomics, LLC
<120>SYSTEMS, COMPOSITIONS, AND METHODS FOR DISCOVERY OF MSI AND NEOEPITOPES THAT PREDICT SENSITIVITY TO CHECKPOINT INHIBITORS
<130>102402.0011u54
<140 >U.S. Ser. No. 15/292,021
<141>2016-10-12
<150 >U.S. 62/240,494
<151>2015-10-12
<160>20
<170 >PatentIn version 3.5
<210>1
<211>9
<212 >PRT <213> Homo sapiens
<400> 1
Pro Thr Asp Ala His Val Leu Gln Lys 1 5
<210> 2
<211> 9
<212> PRT
<213> Homo sapiens
<400> 2
Pro Ala Asp Ala His Val Leu Gln Lys 1 5 <210> 3 <211> 9 <212> PRT <213> Homo sapiens <400> 3
Leu Leu Leu His Val Leu Ala Ala Leu 1 5 <210> 4 <211> 9 <212> PRT <213> Homo sapiens <400> 4
Leu Leu Leu Arg Val Leu Ala Ala Leu 1 5 <210> 5 <211> 9 <212> PRT <213> Homo sapiens <400> 5
Thr Gln Ser Cys Tyr Asn Tyr Leu Tyr 1 5 <210> 6 <211> 9 <212> PRT <213> Homo sapiens <400> 6
Asn Gln Ser Cys Tyr Asn Tyr Leu Tyr 1 5 <210> 7 <211> 9 <212> PRT <213> Homo sapiens <400> 7
Thr Val Val Arg Trp Ser Val Ala Lys 1 5 <210> 8 <211> 9 <212> PRT <213> Homo sapiens <400> 8
Thr Val Val Arg Trp Ser Ala Ala Lys 1 5 <210> 9 <211> 9 <212> PRT <213> Homo sapiens <400> 9
Arg Thr Gly Val Met Lys Cys Ala Tyr 1 5 <210> 10 <211> 9 <212> PRT <213> Homo sapiens <400> 10
Arg Thr Gly Val Met Ile Cys Ala Tyr 1 5 <210> 11 <211> 9 <212> PRT <213> Homo sapiens <400> 11
Tyr Ile His Thr His Thr Phe Tyr Val 1 5 <210> 12 <211> 9 <212> PRT <213> Homo sapiens <400> 12
Tyr Thr His Thr His Thr Phe Tyr Val 1 5 <210> 13 <211> 9 <212> PRT <213> Homo sapiens <400> 13
Ser Gln Ile Trp Asn Leu Asn Pro Val 1 5 <210> 14 <211> 9 <212> PRT <213> Homo sapiens <400> 14
Ser Gln Ile Arg Asn Leu Asn Pro Val 1 5 <210> 15 <211> 9 <212> PRT <213> Homo sapiens <400> 15
Ser Cys Met Asn Pro Gln Thr Phe Lys 1 5 <210> 16 <211> 9 <212> PRT <213> Homo sapiens <400> 16
Ser Cys Met Asn Pro Gln Lys Phe Lys 1 5 <210> 17 <211> 9 <212> PRT <213> Homo sapiens <400> 17
Lys Leu Ser Leu Pro Glu Ser Leu Lys 1 5 <210> 18 <211> 9 <212> PRT <213> Homo sapiens <400> 18
Lys Leu Pro Leu Pro Glu Ser Leu Lys 1 5 <210> 19 <211> 9 <212> PRT <213> Homo sapiens <400> 19
Ala Met Pro Ser Pro Glu Ala Arg Val 1 5 <210> 20 <211> 9 <212> PRT <213> Homo sapiens <400> 20
Ala Thr Pro Ser Pro Glu Ala Arg Val 1 5

SEQUENCE LISTING

```
<160> NUMBER OF SEQ ID NOS: 20

<210> SEQ ID NO 1
<211> LENGTH: 9
<212> TYPE: PRT
<213> ORGANISM: Homo sapiens

<400> SEQUENCE: 1

Pro Thr Asp Ala His Val Leu Gln Lys
1               5

<210> SEQ ID NO 2
<211> LENGTH: 9
<212> TYPE: PRT
<213> ORGANISM: Homo sapiens

<400> SEQUENCE: 2

Pro Ala Asp Ala His Val Leu Gln Lys
1               5

<210> SEQ ID NO 3
<211> LENGTH: 9
<212> TYPE: PRT
<213> ORGANISM: Homo sapiens

<400> SEQUENCE: 3

Leu Leu Leu His Val Leu Ala Ala Leu
1               5

<210> SEQ ID NO 4
<211> LENGTH: 9
<212> TYPE: PRT
<213> ORGANISM: Homo sapiens

<400> SEQUENCE: 4

Leu Leu Leu Arg Val Leu Ala Ala Leu
1               5

<210> SEQ ID NO 5
<211> LENGTH: 9
<212> TYPE: PRT
```

```
<213> ORGANISM: Homo sapiens

<400> SEQUENCE: 5

Thr Gln Ser Cys Tyr Asn Tyr Leu Tyr
1               5

<210> SEQ ID NO 6
<211> LENGTH: 9
<212> TYPE: PRT
<213> ORGANISM: Homo sapiens

<400> SEQUENCE: 6

Asn Gln Ser Cys Tyr Asn Tyr Leu Tyr
1               5

<210> SEQ ID NO 7
<211> LENGTH: 9
<212> TYPE: PRT
<213> ORGANISM: Homo sapiens

<400> SEQUENCE: 7

Thr Val Val Arg Trp Ser Val Ala Lys
1               5

<210> SEQ ID NO 8
<211> LENGTH: 9
<212> TYPE: PRT
<213> ORGANISM: Homo sapiens

<400> SEQUENCE: 8

Thr Val Val Arg Trp Ser Ala Ala Lys
1               5

<210> SEQ ID NO 9
<211> LENGTH: 9
<212> TYPE: PRT
<213> ORGANISM: Homo sapiens

<400> SEQUENCE: 9

Arg Thr Gly Val Met Lys Cys Ala Tyr
1               5

<210> SEQ ID NO 10
<211> LENGTH: 9
<212> TYPE: PRT
<213> ORGANISM: Homo sapiens

<400> SEQUENCE: 10

Arg Thr Gly Val Met Ile Cys Ala Tyr
1               5

<210> SEQ ID NO 11
<211> LENGTH: 9
<212> TYPE: PRT
<213> ORGANISM: Homo sapiens

<400> SEQUENCE: 11

Tyr Ile His Thr His Thr Phe Tyr Val
1               5

<210> SEQ ID NO 12
<211> LENGTH: 9
<212> TYPE: PRT
<213> ORGANISM: Homo sapiens
```

```
<400> SEQUENCE: 12

Tyr Thr His Thr His Thr Phe Tyr Val
1               5

<210> SEQ ID NO 13
<211> LENGTH: 9
<212> TYPE: PRT
<213> ORGANISM: Homo sapiens

<400> SEQUENCE: 13

Ser Gln Ile Trp Asn Leu Asn Pro Val
1               5

<210> SEQ ID NO 14
<211> LENGTH: 9
<212> TYPE: PRT
<213> ORGANISM: Homo sapiens

<400> SEQUENCE: 14

Ser Gln Ile Arg Asn Leu Asn Pro Val
1               5

<210> SEQ ID NO 15
<211> LENGTH: 9
<212> TYPE: PRT
<213> ORGANISM: Homo sapiens

<400> SEQUENCE: 15

Ser Cys Met Asn Pro Gln Thr Phe Lys
1               5

<210> SEQ ID NO 16
<211> LENGTH: 9
<212> TYPE: PRT
<213> ORGANISM: Homo sapiens

<400> SEQUENCE: 16

Ser Cys Met Asn Pro Gln Lys Phe Lys
1               5

<210> SEQ ID NO 17
<211> LENGTH: 9
<212> TYPE: PRT
<213> ORGANISM: Homo sapiens

<400> SEQUENCE: 17

Lys Leu Ser Leu Pro Glu Ser Leu Lys
1               5

<210> SEQ ID NO 18
<211> LENGTH: 9
<212> TYPE: PRT
<213> ORGANISM: Homo sapiens

<400> SEQUENCE: 18

Lys Leu Pro Leu Pro Glu Ser Leu Lys
1               5

<210> SEQ ID NO 19
<211> LENGTH: 9
<212> TYPE: PRT
<213> ORGANISM: Homo sapiens

<400> SEQUENCE: 19
```

```
Ala Met Pro Ser Pro Glu Ala Arg Val
1               5

<210> SEQ ID NO 20
<211> LENGTH: 9
<212> TYPE: PRT
<213> ORGANISM: Homo sapiens

<400> SEQUENCE: 20

Ala Thr Pro Ser Pro Glu Ala Arg Val
1               5
```

What is claimed is:

1. A method of treating a patient having a cancer using immunotherapy, the method comprising:
    comparing genomic sequences of tumor tissue from the patient and a matched normal tissue from the patient to identify at least 50 missense mutation based patient-specific and tumor-specific neoepitopes that have a binding affinity to an HLA type of the patient and
    administering a treatment comprising an effective amount of a checkpoint inhibitor to the patient:
    wherein the at least 50 neoepitopes each have a binding affinity of less than 500 nM; and
    wherein the neoepitopes are peptides having a length of 5 to 30 amino acids.

2. The method of claim 1 wherein theplurality of missense mutations have been selected from each of the neoepitopes using a plurality of distinct individual neoepitope sequences in which a changed amino acid has a distinct position within the neoepitope sequence.

3. The method of claim 2 wherein the individual neoepitope sequences have a length of between 7 and 20 amino acids.

4. The method of claim 1 wherein the missense mutations are filtered by at least one of an a priori known molecular variation selected from the group consisting of a single nucleotide polymorphism, a short deletion and insertion polymorphism, a microsatellite marker, a short tandem repeat, a heterozygous sequence, a multinucleotide polymorphism, and a named variant.

5. The method of claim 1 wherein the high-affinity HLA-matched neoepitopes have been identified by determining affinity of the neoepitopes to at least one MHC Class I sub-type and to at least one MHC Class II sub-type of the patient.

6. The method of claim 5, further comprising a determination of expression level of the neoepitopes.

7. The method of claim 1 wherein the high-affinity HLA-matched neoepitopes have an affinity to at least one MHC Class I sub-type or to at least one MHC Class II sub-type of the patient of equal or less than 150 nM.

8. The method of claim 1 further comprising a step of filtering the HLA-matched neoepitopes by a mutation signature.

9. The method of claim 8 wherein the mutation signature is a signature characteristic for UV-induced DNA damage or smoking-induced DNA damage.

10. The method of claim 1, wherein at least 100 HLA-matched neoepitopes each have the binding affinity of less than 500 nM.

11. The method of claim 10 wherein the at least 100 HLA-matched neoepitopes have an affinity to at least one MHC Class I sub-type or to at least one MHC Class II sub-type of the patient of equal or less than 150 nM.

12. The method of claim 1 further comprising a step of determining microsatellite instability (MSI) in the diseased tissue.

13. The method of claim 1 further comprising a step of determining defective mismatch repair (MMR) in the diseased tissue.

14. The method of claim 1 wherein the checkpoint inhibitor is a CTLA-4 inhibitor or a PD-1 inhibitor.

* * * * *